(12) United States Patent
Nord et al.

(10) Patent No.: US 8,284,897 B2
(45) Date of Patent: Oct. 9, 2012

(54) METHOD AND APPARATUS TO FACILITATE TREATING A TARGET PORTION OF A PATIENT'S BODY WITH RADIATION

(75) Inventors: Janne Nord, Espoo (FI); Ramin Baghaie, Espoo (FI); Marko Rusanen, Helsinki (FI); Juha Kauppinen, Espoo (FI)

(73) Assignee: Varian Medical Systems International AG, Zug (CH)

( * ) Notice: Subject to any disclaimer, the term of this patent is extended or adjusted under 35 U.S.C. 154(b) by 345 days.

(21) Appl. No.: 12/694,010

(22) Filed: Jan. 26, 2010

(65) Prior Publication Data
US 2011/0182409 A1 Jul. 28, 2011

(51) Int. Cl.
*A61N 5/10* (2006.01)
(52) U.S. Cl. .......................................... 378/65
(58) Field of Classification Search .................. 378/64, 378/65
See application file for complete search history.

(56) References Cited

U.S. PATENT DOCUMENTS 7,636,420 B2 * 12/2009 Spies et al. ...................... 378/65
7,894,571 B2 * 2/2011 Keall et al. ......................... 378/8

OTHER PUBLICATIONS

Johnson et al., "Functional Imaging of the Lung," Nature Medicine, vol. 2, No. 11, Nov. 1996, p. 1192.
Ueda et al., "Quantitative Computed Tomography for the Prediction of Pulmonary Function After Lung Cancer Surgery: A Simple Method Using Simulation Software," European Journal of Cardio-thoracic Surgery, 35 (2009), pp. 414-418.

* cited by examiner

*Primary Examiner* — Jurie Yun
(74) *Attorney, Agent, or Firm* — Fitch, Even, Tabin & Flannery, LLP

(57) ABSTRACT

One accesses information regarding the functionality of portions of the patient's body and then uses that information to optimize a radiation-treatment plan to treat a target portion of the patient's body while minimizing at least some collateral radiation-based damage to non-targeted functional portions of the patient's body. By one approach, the aforementioned information can comprise a functionality model as pertains to at least some portions of the patient's body. As one example in these regards, this can comprise optimizing the radiation-treatment plan such that the planned radiation beams tend to pass through non-targeted less-functional portions of the patient's body rather than through non-targeted portions of the patient's body of greater functionality.

24 Claims, 2 Drawing Sheets

METHOD AND APPARATUS TO FACILITATE TREATING A TARGET PORTION OF A PATIENT'S BODY WITH RADIATION

TECHNICAL FIELD

This invention relates generally to the treatment of living tissue with radiation.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

This has led, for example, to the use of collimators to attempt to restrict the profile of the radiation beam in a way that avoids untargeted tissue to the sides of the targeted area. Unfortunately, this practice does not address the entire problem space. As one example in these regards, the radiation beam must typically pass through untargeted tissue on the journey to the targeted area.

Many treatment plans provide for exposing the target volume to radiation from a number of different directions. Arc therapy, for example, comprises one such approach. This approach not only permits radiating the target from a variety of different angles, it also helps to avoid radiating any specific non-targeted portion of the patient's body for the entire treatment period. Though truly beneficial, this approach alone may not be necessarily optimum for all application settings. When treating a target that is adjacent to particularly sensitive non-targeted portions of the patient's body, for example, even this reduced level of exposure may be a cause for concern.

BRIEF DESCRIPTION OF THE DRAWINGS

The above needs are at least partially met through provision of the method and apparatus to facilitate treating a target portion of a patient's body with radiation described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, one accesses information regarding the functionality of portions of the patient's body and then uses that information to optimize a radiation-treatment plan to treat a target portion of the patient's body while minimizing at least some collateral radiation-based damage to non-targeted functional portions of the patient's body. By one approach, the aforementioned information can comprise a functionality model as pertains to at least some portions of the patient's body.

As one example in these regards, this can comprise optimizing the radiation-treatment plan such that the planned radiation beams tend to pass through non-targeted less-functional portions of the patient's body rather than through non-targeted portions of the patient's body of greater functionality.

These teachings will accommodate a range of functionality-assessment metrics and modalities. Relative functionality can be assessed where impaired functionality derives from a disease process, structural design, or even prior or prospective radiation-based damage.

Using these teachings will tend to emphasize the avoidance of exposing otherwise healthy portions of the patient's body to radiation during a radiation-based treatment of a targeted portion of the patient's body. These teachings achieve this beneficial result, by one approach, by referring at least some of the collateral radiation-based damage to less-functional portions of the patient's body. These results are attained without requiring new hardware (such as new collimators) and can be readily implemented via changes to existing radiation-treatment optimization programs. These approaches are economically deployed and are highly scalable as they can be used with a wide variety of differently shaped and differently sized radiation-treatment targets and methodologies.

Figure 1:
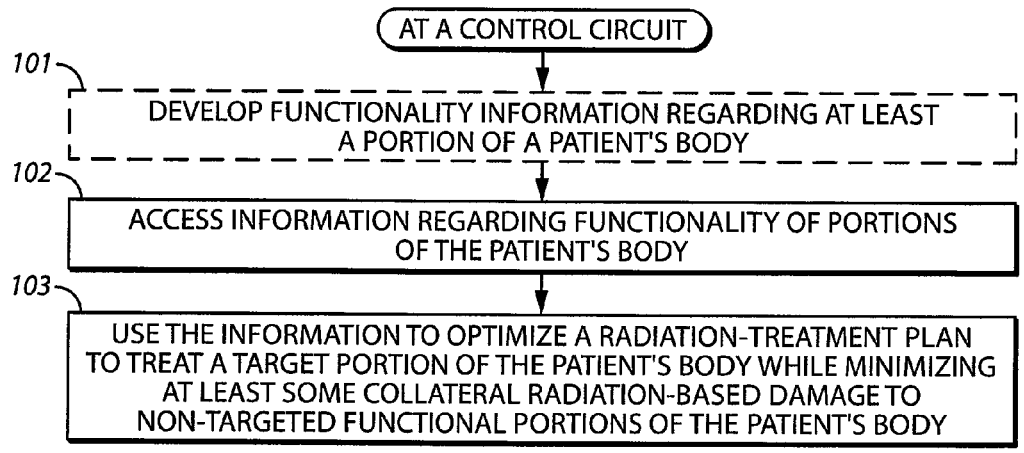
FIG. 1 comprises a flow diagram as configured in accordance with various embodiments of the invention.

These and other benefits may become clearer upon making a thorough review and study of the following detailed description. Referring now to the drawings, and in particular to FIG. 1, an illustrative process 100 that is compatible with many of these teachings will now be presented. A control circuit of choice can carry out this process 100 as desired.

As an optional precursor, this process 100 will accommodate the optional step 101 of developing functionality information regarding at least a portion of a patient's body. This "functionality" refers, at the least, to a relative degree by which a given portion of the patient's body performs its biological function. By one approach, and by way of example, in a given segment of lung tissue the gas-exchanging functionality of the alveoli may be fully unimpaired in which case the functionality of this segment might be viewed as being one hundred percent. As another example, in another given segment of this same lung tissue the gas-exchanging functionality of the alveoli may be partially impaired (due, for example, to a disease process such as emphysema or cancer) such that the gas-exchanging capability is only fifty percent of the first segment's functionality.

The example above measures "functionality" in a purely locally-relative manner, with a local highest level of functionality serving as a benchmark for full functionality. By another approach an objective standard can serve in these regards. Using this approach, the various body portions to be characterized are compared to some external standard of choice.

Such a standard can be based, for example, upon relevant studies of one or more healthy (or selected unhealthy) persons.

There are various approaches one might pursue to effect this step 101. By one approach, for example, computed tomography (CT) (including either three-dimensional CT and/or four-dimensional CT) can serve to develop such information. As one example, CT imaging while using a breathing marker such as O15 can provide functionality information regarding lung tissue. As another example in these regards, one can extract information regarding spatially-located density in lung tissue using a three-dimensional CT image. And as yet a further example in these regards, one can detect compression and decompression information for various portions of a lung using four-dimensional CT imaging.

As another example in these regards, this functionality information can be developed, at least in part, using data pertaining to at least one previously-administered radiation treatment and/or using functionality estimates based upon accumulated (previously-administered and/or subsequently-planned) radiation doses.

As yet another example in these regards, this information regarding functionality can comprise, at least in part, information regarding functionality changes that stem from at least one previously-administered therapy (such as, but not limited to, one or more previously-administered radiation treatments, surgery, and/or medication). By one approach in these regards, such information can be expressed, at least in part, by a model that expresses such functionality changes due to the at least one previously administered therapy.

These examples are intended to serve only in an illustrative capacity. There are, in fact, various known ways to develop functionality information for various portions of the human body and other ways are likely to be developed in the future. Given further that the present teachings are not particularly sensitive to any particular selections in these regards, for the sake of brevity and clarity further elaboration will not be provided here in these regards.

In any event, and regardless of how and when initially obtained and developed, step 102 of this process 100 then provides for accessing information regarding the functionality of portions of the patient's body (i.e., the patient having a target portion (such as a tumor) that is to undergo radiation treatment). By one approach, this can comprise accessing information regarding un-targeted biological materials that are proximal to the treatment target and/or that are potentially in the path of a radiation-treatment beam. When the target region comprises a portion of an organ (such as, for the sake of illustration, a lung) this accessed information can pertain to, at the least, other tissue of that organ as surrounds or is otherwise adjacent to the target region.

Figure 2:
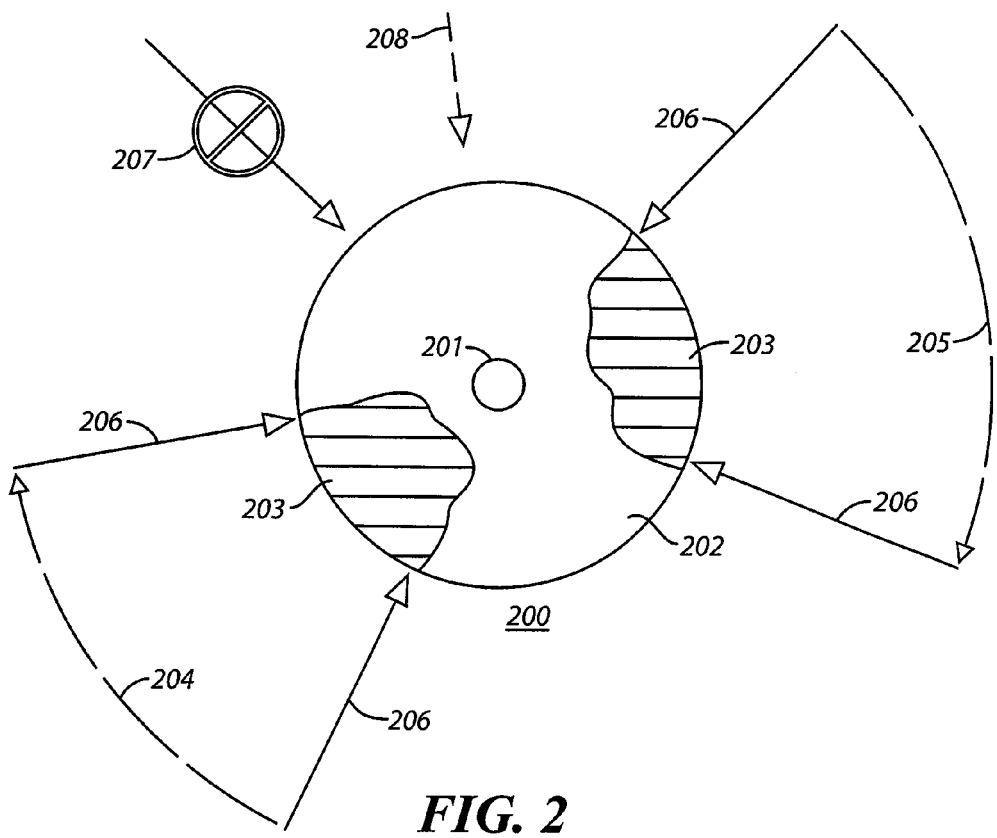
FIG. 2 comprises a schematic view as configured in accordance with various embodiments of the invention.

By one approach this functionality information can assume the form of a functionality model such as a spatial model of functionality. As one very simple illustration in these regards, and without intending any limitations in these regards, FIG. 2 presents a very simple graphic example of such a model. In this model 200 of a given organ, a target region 201 is surrounded by non-targeted material 202.

In this example the bulk of the un-targeted material is shown as being fully functional. Per the dictates of the model, this might mean, for example, that this material ranges somewhere between one hundred percent functional to, say, fifty percent functional. Two portions 203 of the un-targeted material, however, are shown with cross hatching. In this example, this serves to indicate that this material is less than fifty percent functional.

In this simple example, the model simply indicates, in a spatially-correlated manner, which portions of the organ have at least fifty percent functionality and which portions have less than fifty percent functionality. Other model criteria are of course possible. By one approach, for example, four equally-spaced criteria can be employed such as 0-25%, 26-50%, 51-75%, and 76-100% functionality. Generally speaking, the degree of parsed functionality can be broken down to achieve whatever level of granularity may be required to suit the needs of a given application setting.

FIG. 2, of course, comprises only a two-dimensional cross-sectional view of a slice of the organ in question. Such a model can of course comprise additional information that serves to provide a complete three-dimensional view of the organ if desired.

Referring again to FIG. 1, and as alluded to earlier, the functionality of various portions of the patient's body can vary in response to a variety of processes, stresses, and influences. For example, less-functional portions of the patient's body can be less functional due to a corresponding disease process that affects (or has affected) the patient's body.

As another example, less-functional portions of the patient's body can be less functional due to a corresponding structural design of the patient's body. This view can be particularly relevant when comparing various portions of the patient's body against one another using an evaluation criterion that favors some portions to the exclusion of other portions. As one simple example in these regards, when considering different portions of a lung, the primary bronchi is a primary air pathway that is, relatively speaking, empty whereas tissue containing bronchioles is relatively densely packed. When measured only by the functionality criterion of gas-exchanging capability, the latter is considerably more "functional" than the former.

As yet a further example in these regards, less-functional portions of the patient's body can be less functional due to corresponding exposure to radiation-based damage. By one approach, this reduction in functionality can be based upon prior empirical studies of functionality-reduction due to radiation treatment. Such external data can serve, in turn, to estimate a corresponding reduction of local functionality in a given patient who has, is, or will be undergoing a similar treatment process.

At step 103, this process 100 then uses the foregoing information to optimize a radiation-treatment plan to treat the target portion of the patient's body while minimizing at least some collateral radiation-based damage to non-targeted functional portions of the patient's body. Such plans are often optimized by using an iterative calculation process. Beginning with some initial set of treatment-parameter settings, a radiation-treatment planning apparatus iteratively adjusts one or more of those settings and assesses the relative worth of the adjusted plan. It will be understood that the expression "optimizing" should not be confused with the idea of identifying an objectively "optimum" plan that is superior to all other possible plans. Instead, such optimization comprises iteratively assessing alternatives to a given plan to typically identify a series of successively-better plans.

By one approach, such optimization can comprise calculating a comparison of collateral radiation-based damage to both non-targeted functional and less-functional portions of the patient's body as corresponds to a given candidate treatment plan. These calculations, in turn, can be based, if desired, upon use of a model of radiation effects on the patient's body as corresponds to the given candidate treatment plan. There are various ways by which such a comparison can be carried out. By one approach, this can comprise using an objective function value of choice that serves to represent overall effectiveness of a given candidate treatment plan to minimize collateral radiation-based damage to the non-targeted functional portions of the patient's body.

As one illustrative example in these regards, an objective function O describing how the functionality F depends on dose D could be represented as follows:

$$0 <= F <= 1,$$

where F=0 is fully non-functional and F=1 is fully functional and E equals a multiplicative effect of dose D on functionality F, such that E=1 for D=0 and E=0 when D exceeds the cut-off dosage ($D_{cutOff}$). In this illustrative model the patient's tissue becomes fully non-functional after the cut-off dose. This function E is therefore seen to decrease between D=0 and $D_{cutOff}$.

For each point i in the tissue (and with D(i) representing the dose at point i and F(i) representing the original functionality at point i):

$$O_F(i) = -E(D(i)) \cdot F(i)$$

from which the functional part of the objective function becomes:

$$O_F = \Sigma_i O_F(i).$$

It will be understood that this only represents a partial contribution to the total objective function that also describes how well the other objectives (e.g. dose volume objectives for the target and critical organs) are fulfilled. The functional part of the total objective function could be an additive or multiplier to other parts of the total objective function. For example:

$$O_{total} = O_{target} + O_{criticalOrgans} + O_F$$

or $$O_{total} = O_{target} + O_F \cdot O_{criticalOrgans}$$

or $$O_{total} = O_F \cdot [O_{target} + O_{criticalOrgans}].$$

By another approach, one could use functionality-volume histograms (analogous to dose-volume histograms) as objectives to the optimization process. For example, the user could set an objective that "more than 50% of the right lung should have functionality over 90%." Or, "a liver shall have at least 100 cm³ of connected volume (i.e., one continuous volume) of functional tissue."

Many radiation-treatment plans pertain to radiation-treatment platforms that are capable of movement during the treatment itself (such as arc therapy platforms). Such plans often comprise a sequence of control points that define various settings for various treatment platform parameters at various physical locations during the treatment process. In such a case, if desired, the aforementioned step 103 can comprise developing comparisons of the collateral damage of concern at various segments of each given candidate treatment plan. Using this approach, each treatment plan can be evaluated and compared as a function of the aggregated overall ability of the plan to minimize such collateral damage to non-targeted functional portions of the patient's body.

As noted earlier, by one approach this optimization can comprise urging the plan towards an approach that tends to refer at least some of collateral radiation-based damage from non-targeted functional portions to less-functional portions of the patient's body. This can be achieved, for example, by favoring plans that arrange for radiation beams to tend to pass through the less-functional portions of the patient's body rather than through the functional areas of the patient's body.

Referring again to FIG. 2, in this illustrative example the existence of the two areas of less-functional non-targeted portions 203 can lead to an optimized radiation-treatment plan that restricts the application of radiation to occurring within two separate corresponding ranges 204 and 205. Radiation beams 206 directed inwardly to the target 201 will traverse non-targeted content that largely comprises, to the extent possible, less-functional portions of the patient's body. So configured, radiation beams outside these two ranges 204 and 205) are prohibited (as symbolized here by the prohibition symbol denoted by reference numeral 207).

In lieu of the foregoing, or in combination therewith, by another approach radiation beams outside the aforementioned ranges 204 and 205 may not be precluded, but the intensity of the radiation beams may be adjusted accordingly. For example, radiation beams 208 that occur outside these ranges 204 and 205 may have only half the intensity of radiation beams 206 that are within these ranges 204 and 205. Such an approach may be useful, for example, where the geometries of the application setting require that at least some radiation be applied to the target 201 using an otherwise non-optimum directionality.

FIG. 2 can also serve to illustrate yet another approach that is consistent with these teachings. In this example, there are two separated areas that include less-functional biological material. In a case where a sufficient radiation dose can be administered by restricting the radiation beams to only one of these areas, a comparison can be made regarding which of these two areas results in the least collateral harm to non-targeted functional body portions. In this simple example, the less-functional area on the left side of the drawing extends more deeply inwards towards the target 201 than the less-functional area on the right side of the drawing. As a result, radiation beams passing through the less-functional area on the left side of the drawing will exit and pass through a relatively smaller length of non-targeted functional biological material before encountering the target 201. Such a comparative analysis and result can therefore prompt using only the range 204 on the left side of the drawing for the resultant radiation-treatment plan.

Although the preceding discussion has focused on referring radiation to less functional portions of non-targeted organs, the present invention is more general insofar as it encompasses accounting for functionality in optimization of a treatment plan. As yet another approach in these regards, and again by way of illustration, the aforementioned reference to minimization of damage may also refer to estimating the functionality of a whole organ (viewed in the aggregate and not in some parsed manner) after delivery of one or more radiation treatments. In this case, results that yield better overall functionality of the whole organ (or other body part) is preferred instead of looking at the segregated functionality of various parts of the organ. Such an approach can be useful in application settings when it may be beneficial to irradiate healthier (more functional) un-targeted portions of a given body part (such as a lung or spine) to the extent that such an approach yields, in the end, an overall body part having a least-impaired functionality. In some cases, the overall functionality of an organ may not need to be determined as part of the process and in general the invention may be used to refer radiation based on tissue functionality. As a further example, in some cases, the present invention may be practiced to protect less functional portions of an organ. For example, where an organ has pre-existing damage and/or damage due to radiation either delivered or to be delivered, such that such portion should not sustain further damage, the present invention may be used to minimize radiation to such portion to the extent possible.

Figure 3:
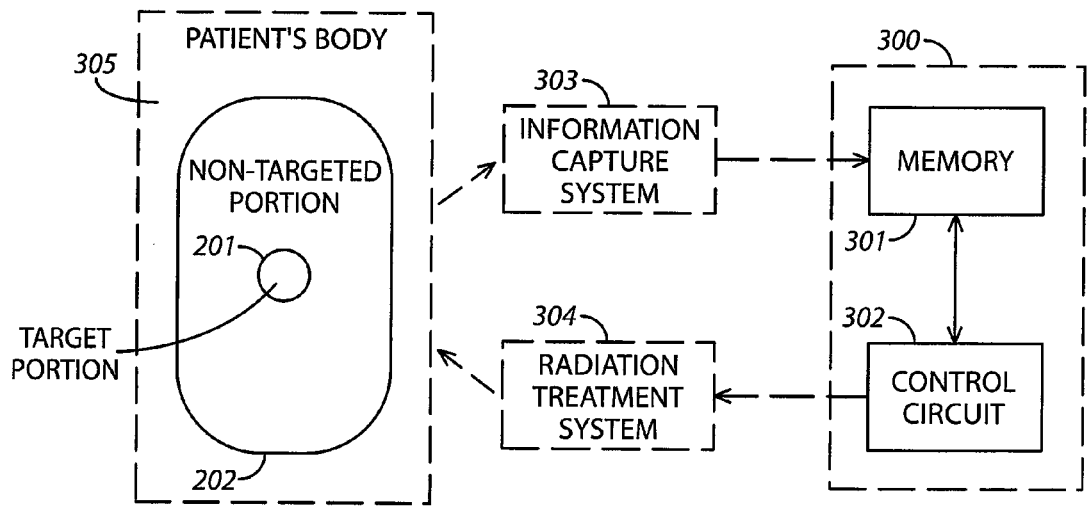
FIG. 3 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 3, an illustrative approach to such a platform 300 will now be provided.

In this illustrative example, the platform 300 comprises a memory 301 that operably couples to a control circuit 302. The memory 301 can comprise a non-transitory computer-readable storage medium of choice. This memory 301 serves to store information regarding functionality of at least portions of a patient's body 305. In the case where the control circuit 302 comprises a partially or wholly programmable platform, this memory 301 can also serve to store computer instructions which, when executed by the control circuit 302, will cause the latter to perform one or more of the steps, actions, and/or functionality as are presented herein.

The control circuit 302 can comprise a fixed-purpose hard-wired platform or can comprise a partially or wholly programmable platform. All of these architectural options are well known and understood in the art and require no further description here.

By one approach, an information capture system 303 (such as, but not limited to, a three-dimensional or four-dimensional CT system, a positron emission tomography (PET) system, and so forth) can serve to provide at least some of the functionality information stored by the memory 301. Also if desired, a radiation treatment system 304 of choice (such as, but not limited to, an arc therapy system) can administer the optimized radiation-treatment plan developed by the control circuit 302.

Such a system may be comprised of a plurality of physically distinct elements as is suggested by the illustration shown in FIG. 3. It is also possible, however, to view this illustration as comprising a logical view, in which case one or more of these components can be enabled and realized via a shared platform.

It will be recognized that these teachings are highly flexible and will accommodate a wide range of variations in practice. For example, by one approach, such a control circuit 302 can be configured to access a functionality model as pertains to at least a portion of a given patient's body and use this functionality model to estimate tissue functionality following at least one given radiation-treatment dose to effect the described assessment and comparison activity.

By taking into account that not all biological material surrounding a given radiation-treatment target is equal in terms of present or resultant functionality, these teachings permit a therapeutically-satisfactory radiation-treatment plan to be optimized in a manner that tends to spare functional non-targeted portions from collateral radiation-based damage. That, at least in some cases, this comes at the expense of diverting such collateral radiation-based damage to less-functional portions will often be an acceptable compromise.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate treating a target portion of a patient's body with radiation, the method comprising:
at a control circuit:
accessing information regarding functionality of portions of the patient's body;
using the information to optimize a radiation-treatment plan to treat the target portion of the patient's body while minimizing at least some collateral radiation-based damage to non-targeted functional portions of the patient's body by referring at least some of the collateral radiation-based damage to less-functional portions of the patient's body.

2. The method of claim 1 wherein the targeted portion of the patient's body comprises a portion of an organ and wherein at least one of the non-targeted functional portions of the patient's body comprises another portion of the organ.

3. The method of claim 1 further comprising:
using computed tomography (CT) to develop the information.

4. The method of claim 3 wherein the CT comprises at least one of:
three-dimensional CT; and
four-dimensional CT.

5. The method of claim 1 further comprising:
using positron emission technology (PET) to develop the information.

6. The method of claim 1 wherein optimizing a radiation-treatment plan comprises, at least in part, planning a plurality of radiation beams that tend to pass through the less-functional portions of the patient's body rather than through the functional portions of the patient's body.

7. The method of claim 1 wherein at least some of the less-functional portions of the patient's body are less functional due to a disease process affecting the patient's body.

8. The method of claim 1 wherein at least some of the less-functional portions of the patient's body are less functional due to a structural design of the patient's body.

9. The method of claim 1 wherein at least some of the less-functional portions of the patient's body are less functional due to radiation-based damage.

10. The method of claim 1 wherein accessing information regarding functionality of portions of the patient's body comprises, at least in part, developing the information using data pertaining to at least one previously-administered radiation treatment.

11. The method of claim 1 wherein accessing information regarding functionality of portions of the patient's body comprises, at least in part, accessing a spatial model of functionality.

12. The method of claim 1 wherein accessing information regarding functionality of portions of the patient's body comprises, at least in part, using information regarding functionality changes stemming from at least one previously administered therapy.

13. The method of claim 12 wherein the at least one previously administered therapy comprises at least one of:
a radiation treatment;
surgery; and
medication.

14. The method of claim 12 wherein using information regarding functionality changes stemming from at least one previously administered therapy comprises, at least in part, using a model that expresses functionality changes due to the at least one previously administered therapy.

15. A method to facilitate treating a target portion of a patient's body with radiation, the method comprising:
at a control circuit:
accessing information regarding functionality of portions of the patient's body by, at least in part, developing the information using functionality estimates based upon accumulated radiation doses;

using the information to optimize a radiation-treatment plan to treat the target portion of the patient's body while minimizing at least some collateral radiation-based damage to non-targeted functional portions of the patient's body.

16. An apparatus to facilitate treating a target portion of a patient's body with radiation, the apparatus comprising:

a memory having information stored therein regarding functionality of portions of the patient's body;

a control circuit operably coupled to the memory and being configured to optimize a radiation-treatment plan to treat the target portion of the patient's body while minimizing at least some collateral radiation-based damage to non-targeted functional portions of the patient's body, at least in part, by referring at least some of the collateral radiation-based damage to non-targeted less-functional portions of the patient's body.

17. The apparatus of claim 16 wherein the control circuit is configured to optimize the radiation-treatment plan by, at least in part, planning a plurality of radiation beams that tend to pass through the non-targeted less-functional portions of the patient's body rather than through the non-targeted functional portions of the patient's body.

18. The apparatus of claim 16 wherein the information, at least in part, comprises a functionality model.

19. The apparatus of claim 16 wherein the control circuit is configured to optimize the radiation-treatment plan while minimizing at least some collateral radiation-based damage to non-targeted functional portions of the patient's body by at least in part, calculating a comparison of collateral radiation-based damage to both non-targeted functional and less-functional portions of the patient's body as corresponds to a given candidate treatment plan.

20. The apparatus of claim 19 wherein the control circuit is further configured to calculate the comparison, at least in part, by using a model of radiation effects on the patient's body as corresponds to the given candidate treatment plan.

21. The apparatus of claim 16 wherein the control circuit is further configured to optimize the radiation-treatment plan to treat the target portion of the patient's body while minimizing at least some collateral radiation-based damage to non-targeted functional portions of the patient's body by using an objective function value that represents overall effectiveness of a given candidate treatment plan to minimize collateral radiation-based damage to the non-targeted functional portions of the patient's body.

22. The apparatus of claim 16 wherein the control circuit is further configured to optimize the radiation-treatment plan to treat the target portion of the patient's body while minimizing at least some collateral radiation-based damage to non-targeted functional portions of the patient's body by developing comparisons of such damage at various segments of a given candidate treatment plan.

23. A non-transitory computer-readable storage medium having computer instructions stored therein, which computer instructions when executed by a digital computing platform provide for:

accessing information regarding functionality of a patient's body having a target portion that is to be treated with radiation;

optimizing a radiation-treatment plan to treat the target portion of the patient's body while minimizing at least some collateral radiation-based damage to non-targeted functional portions of the patient's body by referring the collateral radiation-based damage to non-targeted less-functional portions of the patient's body.

24. The non-transitory computer-readable storage medium of claim 23 wherein optimizing a radiation-treatment plan comprises, at least in part, planning a plurality of radiation beams that tend to pass through the non-targeted less-functional portions of the patient's body rather than through the non-targeted functional portions of the patient's body.

* * * * *